(12) United States Patent
Rushing et al.

(10) Patent No.: US 11,528,904 B2
(45) Date of Patent: Dec. 20, 2022

(54) MODULAR BLOOD PRODUCT STORAGE SYSTEM FOR TEMPERATURE-REGULATED STORAGE OF BLOOD PRODUCTS

(71) Applicant: B Medical Systems S.A. R.L., Hosingen (LU)

(72) Inventors: Alan Rushing, Mont-Saint-Guibert (BE); Marc Foyen, Mont-Saint-Guibert (BE)

(73) Assignee: B MEDICAL SYSTEMS S.A.R.L., Hosingen (LU)

( * ) Notice: Subject to any disclaimer, the term of this patent is extended or adjusted under 35 U.S.C. 154(b) by 0 days.

(21) Appl. No.: 16/315,755

(22) PCT Filed: Jul. 3, 2017

(86) PCT No.: PCT/EP2017/066529
§ 371 (c)(1),
(2) Date: Jan. 7, 2019

(87) PCT Pub. No.: WO2018/010999
PCT Pub. Date: Jan. 18, 2018

(65) Prior Publication Data
US 2019/0364884 A1 Dec. 5, 2019

(30) Foreign Application Priority Data
Jul. 11, 2016 (DE) ...................... 10 2016 212 609.1

(51) Int. Cl.
*A01N 1/02* (2006.01)
*A61M 1/02* (2006.01)

(52) U.S. Cl.
CPC ......... *A01N 1/0252* (2013.01); *A01N 1/0242* (2013.01); *A61M 1/0254* (2014.02);
(Continued)

(58) Field of Classification Search
CPC . A01N 1/0252; A01N 1/0242; A61M 1/0286; A61M 1/0254; A61M 1/0277;
(Continued)

(56) References Cited

U.S. PATENT DOCUMENTS 2,962,875 A * 12/1960 Barroero ............... F25D 25/028
62/256
3,529,358 A * 9/1970 Robinson .............. F26B 21/026
34/494
(Continued)

FOREIGN PATENT DOCUMENTS

RU  2228735 C2  5/2004
SU  936923 A1  6/1982

OTHER PUBLICATIONS

International Search Report for International application No. PCT/EP2017/066529.
(Continued)

*Primary Examiner* — Kun Kai Ma
(74) *Attorney, Agent, or Firm* — Jerold I. Schneider; Schneider IP Law

(57) ABSTRACT

Modular blood product storage system for temperature-regulated storage of blood products with a temperature regulation unit for temperature regulation of the blood product storage system, a base unit and at least one agitator unit with an upper connection side, a lower connection side, a movable compartment to receive the blood products and a drive for movement of the compartment, wherein the compartment is arranged between the upper connection side and the lower connection side, wherein the upper connection side of the agitator unit is selectively connectable to the temperature regulation unit or a further agitator unit, and
(Continued)

wherein the lower connection side of the agitator unit is selectively connectable to the base unit or a further agitator unit.

16 Claims, 3 Drawing Sheets

(52) U.S. Cl.
CPC ..... *A61M 1/0286* (2014.02); *A61M 2205/362* (2013.01); *A61M 2205/3606* (2013.01); *A61M 2205/505* (2013.01)

(58) Field of Classification Search
CPC .... A61M 2205/3606; A61M 2205/362; A61M 2205/505
See application file for complete search history.

(56) References Cited

U.S. PATENT DOCUMENTS

| | | | | |
|---|---|---|---|---|
| 8,192,983 | B2* | 6/2012 | Kiyota | C12M 41/48 435/303.1 |
| 8,383,395 | B2* | 2/2013 | Hata | C12M 41/14 382/133 |
| 8,778,263 | B2* | 7/2014 | Walker | A61M 1/0277 435/238 |
| 9,579,245 | B2* | 2/2017 | Larkner | G07F 11/165 |
| 2004/0147012 | A1* | 7/2004 | Yokoi | C12M 23/48 435/303.1 |
| 2004/0244396 | A1* | 12/2004 | Lane | A47F 3/0482 62/246 |
| 2006/0093514 | A1* | 5/2006 | Dawes | A01N 1/0278 422/44 |
| 2009/0037031 | A1* | 2/2009 | George | C12M 23/44 700/300 |
| 2009/0111179 | A1* | 4/2009 | Hata | C12M 23/14 435/394 |
| 2011/0281514 | A1* | 11/2011 | Haugen | B08B 15/023 454/57 |
| 2013/0011226 | A1* | 1/2013 | Camenisch | A01N 1/0263 414/277 |
| 2019/0247276 | A1* | 8/2019 | Mongrenier | A61J 1/10 |

OTHER PUBLICATIONS

International Preliminary Report on Patentability for International application No. PCT/EP2017/066529.
Search Report, RU Patent Office, for corresponding application based on PCT/EP2017/066,529 dated Nov. 3, 2020.

* cited by examiner

US 11,528,904 B2

MODULAR BLOOD PRODUCT STORAGE SYSTEM FOR TEMPERATURE-REGULATED STORAGE OF BLOOD PRODUCTS

The present invention relates to a blood product storage system for temperature-regulated storage of blood products. In particular, the invention relates to a storage system for platelet concentrates disposed in bags with an agitator unit for movement of the platelet concentrates. The latter is also known as a shaker or rocker.

Thrombocytes or blood platelets are necessary for various medical applications, e.g. for platelet transfusions. The platelet concentrates or products necessary for this are generally obtained from donated whole blood, filled into special bags and must be stored in accordance with defined requirements. Firstly, the platelet concentrates must be stored at a temperature of +22±2° C. Moreover, the platelet concentrates must be kept in constant movement during storage in order to prevent sedimentation and therefore clumping of the platelets.

In general, special storage systems are used for this, which maintain the temperature in the predetermined range and additionally have an agitator unit, which keeps the platelet concentrates in constant, principally rotating movement. These storage systems often also have a monitoring and alarm system to immediately indicate a deviation in temperature or faults of the agitator unit, so that damage of the platelet concentrates can be prevented by quick action.

Therefore, storage systems are known from the prior art, which consist of an incubator cabinet, in which at least one agitator unit is housed as a separate device. The incubator cabinet has a temperature regulation unit to maintain the temperature inside the cabinet in the necessary range of +22±2° C. The agitator unit generally consists of a base plate with a motion generator, by means of which a frame with several tray-type shelves to receive the platelet concentrates disposed in bags is then set in motion.

Although these storage systems can store the platelet concentrates to a high quality, these are nevertheless associated with some disadvantages. For instance, individual adjustment to the actual storage requirement for platelet concentrates is not possible. If the incubator cabinet provides space for four agitator units each with seven compartments, for example, the entire interior of the incubator cabinet must always be regulated in temperature, even if only one compartment of an agitator unit is filled with platelet concentrates disposed in bags. Moreover, in this case the entire agitator unit must also be operated, i.e. so that all seven compartments are kept in motion by means of the common frame.

Accordingly, it is also a disadvantage if the current storage requirement exceeds the actual space available in the incubator cabinet. In this case, at least a second incubator cabinet with at least one agitator unit must be kept in reserve.

As a result, therefore, there is an increased space requirement overall as well as increased costs because of the still necessary temperature regulation of the entire incubator cabinet and the movement of the entire agitator unit.

It is therefore an object of the present invention to provide a blood product storage system for temperature-regulated storage of blood products, in particular platelet concentrates in bags, which can be adjusted modularly to the actual storage requirement.

The object is achieved with a modular storage system according to claim 1. Advantageous further configurations are described in the dependent claims.

There is proposed according to the invention a modular blood product storage system for temperature-regulated storage of blood products with a temperature regulation unit for temperature regulation of the blood product storage system, a base unit and at least one agitator unit with an upper connection side, a lower connection side, a movable compartment to receive the blood products and a drive for movement of the compartment. According to the invention, the compartment is arranged between the upper connection side and the lower connection side, wherein the upper connection side of the agitator unit is selectively connectable to the temperature regulation unit or a further agitator unit, and wherein the lower connection side of the agitator unit is selectively connectable to the base unit or a further agitator unit. In order words, the agitator unit is configured in such a manner that either a further agitator unit or the temperature regulation unit can be arranged on the upper connection side. Accordingly, the lower connection side is configured in such a manner that either a further agitator unit or the base unit can be arranged thereon.

Therefore, in the simplest case the modular blood product storage system consists of a base unit, precisely one agitator unit arranged thereon and a temperature regulation unit arranged on the agitator unit. In this case, the temperature regulation unit only has to regulate the temperature of the interior of one agitator unit. Moreover, since the agitator unit has its own drive for movement of the compartment, no unnecessary movement of an empty compartment is performed.

In the case where several blood products are to be stored at regulated temperature, a further agitator unit is arranged between the temperature regulation unit and the base unit. Accordingly, in the case of a decrease in storage requirement one agitator unit or several agitator units can also be removed.

Thus, overall, a modular blood product storage system is demonstrated that can be adjusted quickly and simply to the actually existing storage requirement for blood products. Hence, ultimately only the currently necessary space of the blood product storage system is regulated in temperature by the temperature regulation unit in the desired range of, for example, +22±2° C.

Expediently, the temperature regulation unit and/or the base unit has an air circulation device, wherein the air circulation device generates a temperature-regulated air flow between the temperature regulation unit and the base unit. Thus, the blood product storage system can be regulated effectively to the desired temperature of, for example, +22±2° C. For this it is expedient if the temperature regulation unit has elements for cooling and/or heating, so that the desired temperature can be maintained in the blood product storage system irrespective of the ambient temperature. Alternatively, the elements for cooling and/or heating can also be (additionally) provided in the base unit.

It is advantageous if the agitator unit has a bottom provided with openings, wherein the bottom is arranged below the compartment in the region of the lower connection side and the temperature-regulated air flow flows through the openings of the temperature regulation unit to the base unit. This ensures that all the blood products received in the compartment are regulated to the desired temperature. Moreover, it is thus also ensured that a homogeneous temperature regulation is achieved within the blood product storage system, since the temperature-regulated air flow from the temperature regulation unit can flow through several agitator units. In association with this it can also be advantageous if the compartment has passages for the air flow.

Expediently, the agitator unit has a separate air passage, wherein the air flow from the base unit to the temperature regulation unit flows through the air passage. It can thus be assured that any mixture of fresh temperature-regulated air with air already changed in temperature does not adversely affect the temperature inside the blood product storage system. As a result, it is guaranteed that the blood products received in the compartment are regulated to the necessary temperature of, preferably 22±2° C.

It is advantageous if the temperature regulation unit has a power supply, wherein the at least one agitator unit can be supplied with current from the power supply via the upper connection side. In particular, it is advantageous if the power transmission is achieved by means of corresponding contacts or a high-speed coupling. It is advantageous if the agitator unit on the lower connection side also has corresponding elements for power transmission. Thus, a secure power supply can also be guaranteed for a blood product storage system with more than one agitator unit. Alternatively, it is conceivable that the base unit has a power supply, wherein the at least one agitator unit can be supplied via the lower connection side with power from the power supply of the base unit.

Expediently, the agitator unit has an access opening for the insertion and removal of blood products, wherein the access opening can be closed by a door. In particular, it is advantageous if the drive stops when the door is opened. This can firstly prevent too great an influence on the temperature inside the blood product storage system. Thus, there is no need to open a large-surface door leaf, as in the case of an incubator cabinet, but only a door that closes precisely one compartment off from the surrounding area. The access opening necessary for this is correspondingly small. Moreover, a quick and secure removal or insertion of the blood product can also occur as a result of the stoppage of the drive. This is particularly advantageous where each agitator unit has its own drive for movement of its own compartment and stoppage of an agitator unit's drive does not interrupt movement of the moveable compartments of other agitator units.

It is advantageous if the blood product storage system has a control device, wherein the drive of the agitator unit can be actuated on an individual basis by means of the control device. It is expedient in this case if the operating parameters of the drive of the agitator unit are adjustable by means of the control device, in particular the speed and type of movement of the compartment. It is thus possible when using several agitator units to adjust the movement of the compartment of each one of the agitator units separately. Thus, for example, the compartment of one agitator unit can move in a circular motion at a speed of 60 rpm, while the compartment of a further agitator unit is moved elliptically at a speed of 50 rpm. This is particularly advantageous when blood products of different ages are housed in the blood product storage system. In particular, platelet concentrate generally has a life of four days at maximum, wherein the quality decreases with increasing age. The age-related decrease in quality can be counteracted to some extent by the adjustment of the movement according to the invention. Expediently, either the temperature regulation unit or the base unit has the control device.

For actuation of the drive of the agitator unit, the blood product storage system expediently has a modular bus system. The bus system can be configured in parallel to the power supply, so that the upper connection side and the lower connection side of the agitator unit are configured to integrate the agitator unit or a further agitator unit into the bus system. A particularly simple and effective actuation of the individual agitator units of the blood product storage system can occur in this way.

In a further embodiment, the agitator unit has a liquid circuit that is connectable to the temperature regulation unit, wherein the temperature regulation unit has a pump for circulation of the fluid of the liquid circuit. As a result of the liquid circuit of each one of the agitator units it can be guaranteed that even when a plurality of agitator units are used, the temperature in the interior of the blood product storage system remains in the desired range of, notably, 22±2° C. It is particularly expedient if the liquid circuit runs in a meander shape or loops below the compartment in order to achieve an effective temperature regulation of the blood products received in the compartment. It is also conceivable that the circulation pump is housed in the base unit.

It is advantageous if the agitator unit has couplings for the liquid circuit on the lower connection side and/or on the upper connection side. The couplings that are particularly suitable are liquid couplings in the form of high-speed or plug-type couplings, so that the blood product storage system can be supplemented or reduced by one agitator unit quickly and simply when required.

The invention will be explained below on the basis of an exemplary embodiment shown in more detail in the schematic drawings, wherein.

Figure 1:
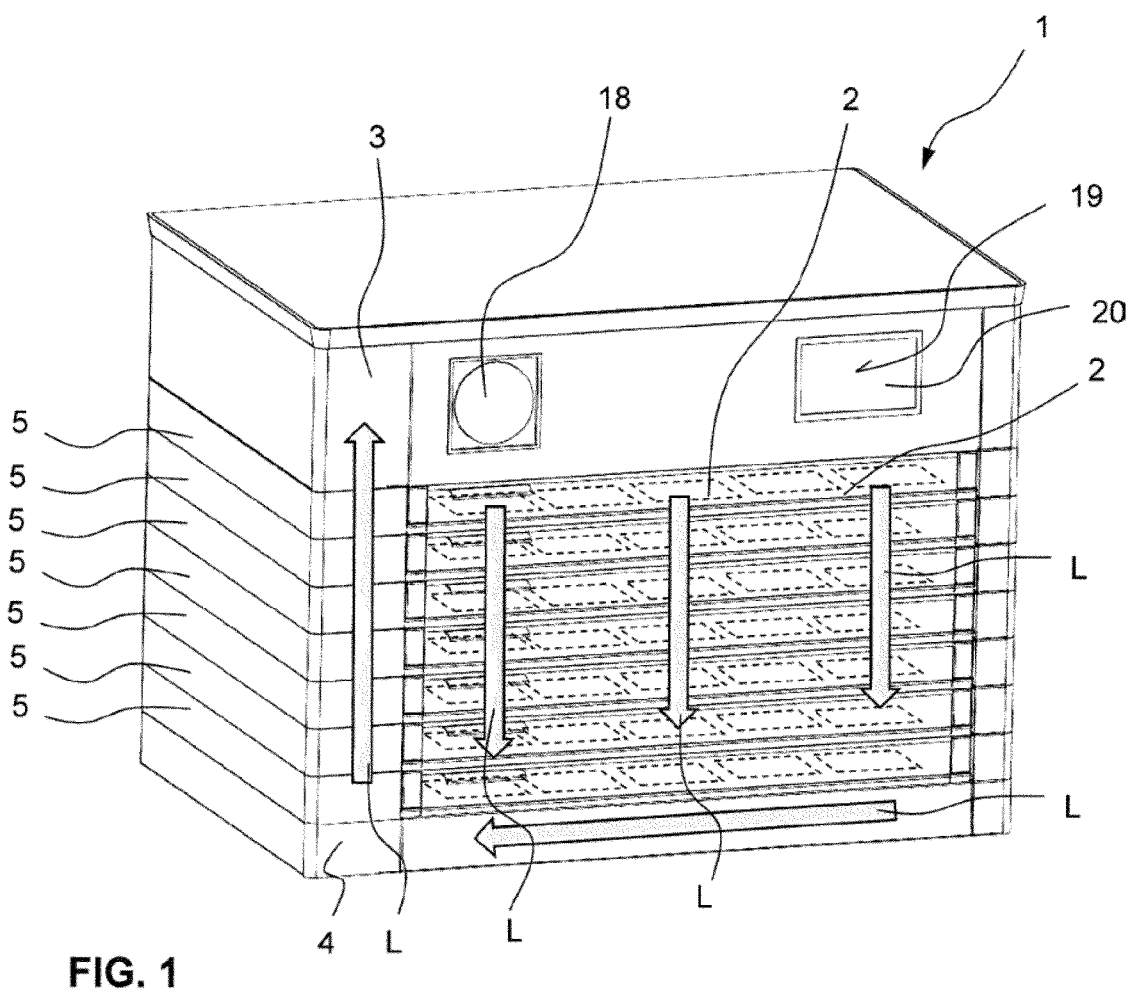
FIG. 1 is a perspective view of a blood product storage system according to the invention with seven agitator units.

FIG. 1 shows a blood product storage system 1 according to the invention for the temperature-regulated storage of blood products 2 with a temperature regulation unit 3, a base unit 4 and, in this exemplary embodiment, seven agitator units 5. In this exemplary embodiment platelet concentrate in bags is provided as blood products 2. The blood product storage system 1 has a layered vertical structure, wherein the base unit 4 forms the bottom unit and the temperature regulation unit 3 the top unit in vertical direction. Moreover, the base unit 4 is conceived to stand the blood product storage system 1 upright, e.g. on a table or the floor. For this, the base unit 4 can have rotating feet (not shown) on the underside to also place the blood product storage system 1 horizontally on uneven support surfaces.

Figure 2:
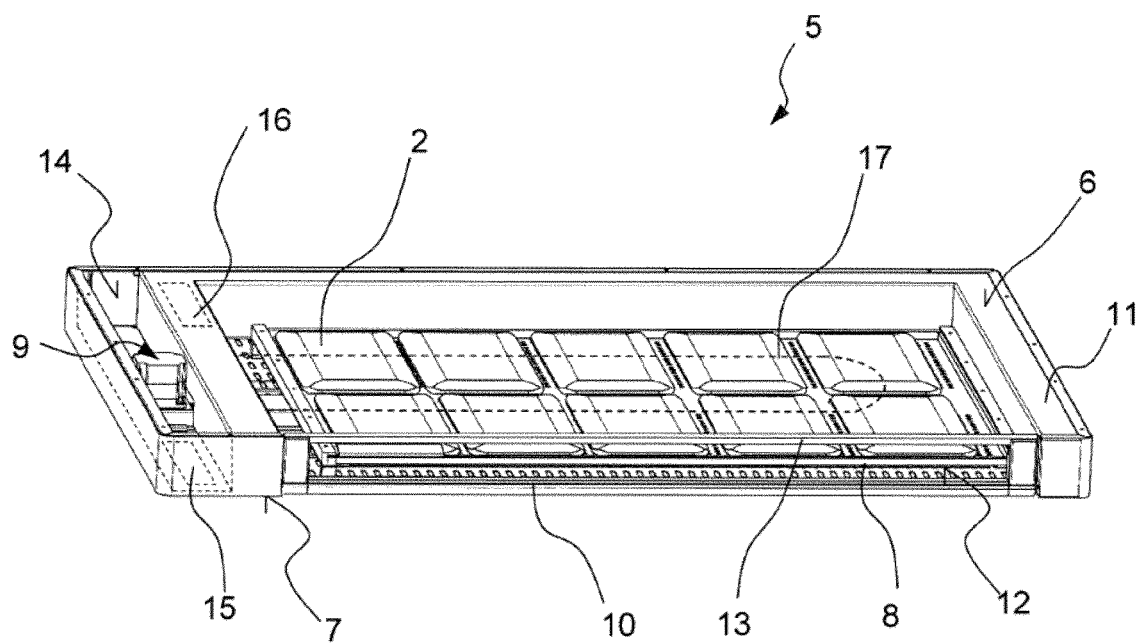
FIG. 2 is a perspective view of an agitator unit.
Figure 3:
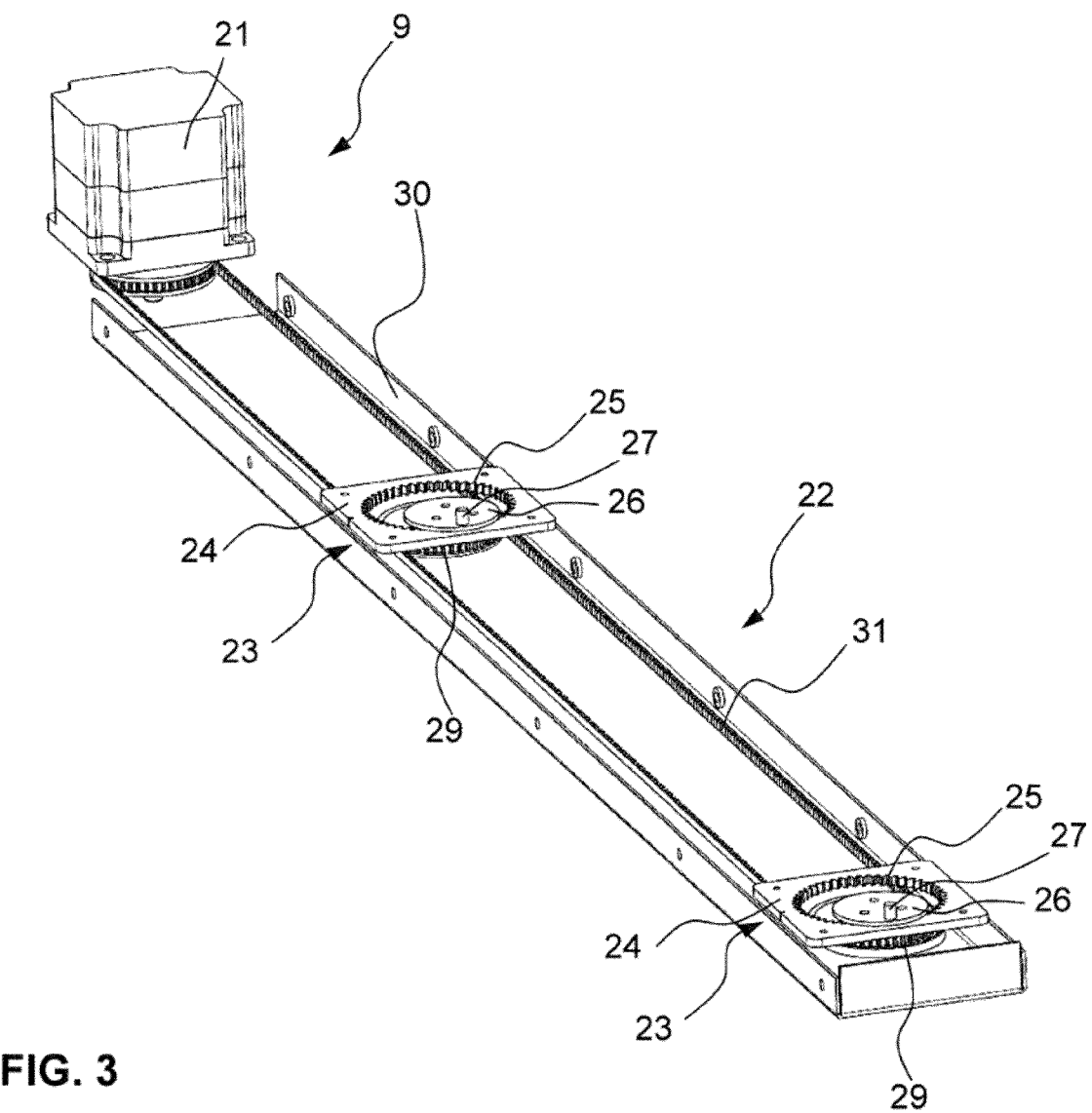
FIG. 3 is perspective view of a drive of an agitator unit.

As shown in FIG. 2, each agitator unit 5 has an upper connection side 6 and a lower connection side 7. In addition, each agitator unit 5 has a compartment 8 for receiving the blood products 2. For movement of the compartment 8 the agitator unit 5 has a drive 9. The compartment 8 is provided with passages, as shown. In addition, the agitator unit 5 has a bottom 10 provided with holes, which is arranged below the compartment 8 in the region of the lower connection side 6. The compartment 8 is surrounded in a U-shape by an insulation 11 so that an access opening 12 is left open for the insertion and removal of blood products 2 into the compartment 8 or from the compartment 8. The access opening 12 can be closed with a door 13. Moreover, the agitator unit 5 has a side chamber 14, in which parts of the drive 9 and also a separate air passage 15 are arranged. The side chamber 14 is separated from the region, in which the compartment 8 is arranged, by the insulation 11.

Each agitator unit 5 has a connection region 16 on the upper connection side 6 and on the lower connection side 7. The connection region 16 serves to connect the agitator unit 5 to a further agitator unit 5, the temperature regulation unit 3 or the base unit 4, as will be explained in more detail below. The connection region 16 has a power coupling, a bus coupling as well as a fluid coupling for connection of a liquid circuit 17 of the agitator unit 5. The liquid circuit 17 of the agitator unit 5 is directed in a loop or meandering shape below the compartment 8 and serves to (additionally) regulate the temperature of the blood products 2 received in the compartment 8.

The temperature regulation unit 3 and/or the base unit 4 has an air circulation device (not shown) for generation of a temperature-regulated air flow L. The temperature-regulated air flow L is represented by arrows in FIG. 1. In this exemplary embodiment the temperature-regulated air flow L is generated by the temperature regulation unit 3. The temperature-regulated air flow L regulates the interior of the blood product storage system 1 to the temperature necessary for platelet concentrates of 22±2° C. by flowing from the temperature regulation unit 3 through the agitator units 5 to the base unit 4. In the base unit 4 the air flow L is then directed laterally in the direction of the side chamber 14 of the agitator units 5, and through the separate air passages 15 of the agitator units 5 from the base unit 4 again in the direction of the temperature regulation unit 3. It can thus be ensured that the blood products 2 are regulated to the desired temperature with freshly temperature-regulated air. To enable or not hinder the air flow L, each agitator unit 5 has passages in the respective compartment 8 as well as the bottom 10 provided with openings.

Moreover, the (additional) liquid circuit 17 of each of the agitator units 5 is provided for temperature regulation of the blood products 2. In particular if the blood product storage system 1 has a relatively high number of agitator units 5 (e.g. 24), regulation to the desired temperature can be ensured by the additional liquid circuit 17. For this, a combined liquid circuit is generated by means of the fluid couplings provided in the connection region 16, into which all the individual liquid circuits 17 of the respective agitator units 5 are incorporated. The temperature regulation unit or the base unit has a pump for circulating the combined liquid circuit. The combined liquid circuit is preferably pre-regulated to the desired temperature by means of an additional temperature regulation element.

The temperature regulation unit 3 additionally has a power supply (not shown), a temperature curve display 18, a control device 19 and also a control panel 20. The control panel 20 is configured as a touch screen in this exemplary embodiment. The temperature curve display 18 shows the current temperature in the interior of the blood product storage system 1 as well as a temperature-time curve. The control device 19 controls all functions of the temperature regulation unit 3 and the incorporated agitator units 5. The power supply in this exemplary embodiment is a conventional 230 V connection, but can also have additional batteries, for example, to also guarantee function of the blood product storage system 1 in the event of a power cut. Moreover, the power supply can also be arranged in the base unit 4.

For construction of the blood product storage system 1 the base unit 4 is firstly erected. The first agitator 5 is placed with the lower connection side 7 onto the base unit 4 and is firmly connected to this, for example, by means of one or more connecting elements. A second agitator unit 5 can then be placed with the lower connection side 7 on the upper connection side 6 of this first agitator unit 5. In this case, the liquid circuit 17 of the first agitator unit 5 is connected to the liquid circuit 17 of the second agitator unit 5 by means of the fluid couplings provided in connection region 16. In addition, a power-carrying connection is created between the first agitator unit 5 and the second agitator unit 5 by means of the contacts provided in the respective connection region 16. A bus connection is also created accordingly by means of a contact or a coupling. A further agitator unit 5 can then be placed with the lower connection side 7 on the upper connection side 6 of the second agitator unit 5 and integrated as just described. The temperature regulation unit 3 is lastly placed on the upper connection side 7 of the last desired agitator unit 5. In this case, the combined liquid circuit is connected to the circulation pump of the temperature regulation unit 3 by means of corresponding fluid couplings. In addition, the power supply of the agitator units 5 is created by a connection with the power supply of the temperature regulation unit 3. Moreover, the agitator units 5 are integrated into a bus system connected to the control device 19.

The entire blood product storage system 1 can now be controlled via the control panel 20. For example, the combined liquid circuit can be activated or deactivated. In addition, the drive 9 of an agitator unit 5 can be actuated selectively, for example, and thus be reduced in speed, for example. In addition, the control panel 20 can also be used to cause the drive 9 of an agitator unit 5 to stop when the door 13 of the access opening 12 is opened. It is also conceivable that the drive 9 is connected to the door 13 by means of a contact switch, so that stoppage of the drive 9 can occur independently of an actuation through the control device 19.

For the modular extension and reduction of the storage capacity of the blood product storage system 1 the temperature regulation unit 3 is firstly removed from the upper connection side 6 of the uppermost agitator unit 5. Either additional agitator units 5 can then be put in place or agitator units 5 can be removed. Once the desired storage capacity has been reached, the temperature regulation unit 3 is placed on the upper connection side 7 of the now uppermost agitator unit 5 again.

The drive 9 of the agitator unit 5 will be described in the following. The drive 9 has an electric motor 21 and a gear system 22. The gear system 22 has two planetary gear units 23. The planetary gear units 23 are identical in structure, so that only one planetary gear unit 23 will be described in more detail below.

The planetary gear unit 23 consists of a planet disc 24 with a toothed internal periphery 25. A planet wheel 26 with a spigot 27 and a toothed external periphery 28 can rotate on the toothed internal periphery 25. The planet disc 24 is fixedly connected to a frame 30 of the drive 9. The planet wheel 26 is driven eccentrically by means of a pulley 29. The pulley 29 is arranged concentrically to the planet disc 24 and connected by means of a belt 31 to a drive wheel 32 connected to the electric motor 21. The belt 31 is configured as a toothed belt here.

As shown, the spigot 27 is arranged eccentrically on the planet wheel 26 and extends in vertical direction from the frame 30. The spigot 27 is connected to the compartment 8 of the agitator unit 5 and transfers the resulting movement to the compartment 8. An elliptical movement of the compartment 8 is achieved as a result of the eccentric arrangement of the planet wheel 26 to the pulley 29 and the eccentric arrangement of the spigot 27 on the planet wheel 26. The type of movement of the compartment 8 can be influenced by changing the relative position of the spigot 27 on the planet wheel 26. As mentioned, an elliptical movement of the compartment 8 results in the case of the illustrated eccentric position of the spigot 27 on the planet wheel 26. A circulating movement of the compartment 8 results in the case of a concentric arrangement of the spigot 27 on the planet wheel 26. In the case of a tangential arrangement of the spigot 27 on the planet wheel 26, i.e. an arrangement substantially in the region of the toothed external periphery 28, there results a linear movement of the compartment 8.

It is conceivable that the movement of the compartment 8 is achieved by replacement of the planet wheels 26 of the planetary gear units 23. Moreover, the spigot 27 can also be moved in position by motor, i.e. by an electric motor in the planet wheel 26 attached to the power supply and the bus system by means of sliding contacts.

LIST OF REFERENCES

1 blood product storage system
2 blood product
3 temperature regulation unit
4 base unit
5 agitator unit
6 upper connection side
7 lower connection side
8 compartment
9 drive
10 bottom
11 insulation
12 access opening
13 door
14 side chamber
15 air passage
16 connection region
17 liquid circuit
18 temperature display
19 control device
20 control panel
21 electric motor
22 gear system
23 planetary gear unit
24 planet disc
25 toothed internal periphery
26 planet wheel
27 spigot
28 toothed external periphery
29 pulley
30 frame
31 belt
L air flow

The invention claimed is:

1. Modular blood platelet storage system for temperature-regulated storage of blood platelet concentrates, the modular blood platelet storage system comprising:
   a. a temperature regulation unit,
   b. a base unit;
   c. a plurality of agitator units arranged between the temperature regulation unit and the base unit;
   d. an air temperature regulation system configured to provide temperature regulated air;
   e. an air circulation device configured to generate a circulating flow of the temperature-regulated air through each of the plurality of agitator units between the temperature regulation unit and the base unit; and
   f. at least one drive;
      wherein each of the plurality of agitator units comprises an upper connection side, a lower connection side, and a movable compartment to receive the blood platelets, the moveable compartment being arranged between the upper connection side and the lower connection side and the moveable compartment being moveable by the at least one drive to agitate blood platelets received in the moveable compartment;
   wherein the lower connection side of each of the plurality of agitator units is configured to be selectively connectable to the base unit or to the upper connection side of another one of the plurality of agitator units;
   wherein the lower connection side of one of the plurality of agitator units is connected to the base unit;
   wherein the upper connection side of each of the plurality of agitator units is configured to be selectively connectable to the temperature regulation unit or to the lower connection side of another one of the plurality of agitator units;
   wherein the upper connection side of one of the plurality of agitator units is connected to the temperature regulation unit;
   wherein the circulating flow of temperature-regulated air has a first portion flowing from the temperature regulation unit to and through the base unit and a second portion flowing from the base unit to and through the temperature regulation unit; and
   wherein one of the first and second portions of the circulating flow of temperature-regulated air flows through the moveable compartment of each of the plurality of agitator units, and the other of the first and second portions of the circulating flow of temperature-regulated air flows through one or more separate air circulation passages so that the one of the first and second portions of the temperature-regulated air that flows through the one or more air circulation passages is separated from the other of the first and second portions of the temperature-regulated air that flows through the moveable compartment of each of the plurality of agitator units; and
   wherein each of the plurality of agitator units has a bottom provided with openings, wherein the bottom is arranged below the moveable compartment in the region of the lower connection side, wherein the first portion of the temperature-regulated air flow flows through the moveable compartment of each of the plurality of agitator units and through the openings of each of the plurality of agitator units.

2. The blood platelet storage system of claim 1,
   wherein each of the plurality of agitator units has one or more separate air passages, and wherein the one or more separate air passage of each of the plurality of agitator units together form the one or more separate air circulation passages of the modular blood platelet storage system;
   wherein the first portion of the circulating flow of temperature-regulated air flows through the moveable compartment of each of the plurality of agitator units, and wherein the first portion of the circulating flow of temperature-regulated air which flows through the moveable compartment of each of the plurality of agitator units flows through the openings of each of the plurality of agitator units; and
   wherein the second portion of the circulating flow of temperature-regulated air flows through the one or more separate air circulation passages of each of the plurality of agitator units which together form the one or more separate air circulation passages of the modular blood platelet storage system.

3. The blood platelet storage system of claim 2, wherein each of the plurality of agitator units has an individual drive for movement of its respective moveable compartment.

4. The blood platelet storage system of claim 2, wherein the individual drive comprises an electric motor.

5. The blood platelet storage system of claim 2, wherein the temperature regulation unit has a power supply, and wherein the upper connection side of each of the plurality of agitator units comprises a power connection connected to the power supply of the temperature regulation unit.

6. The blood platelet storage system of claim 2, wherein the base unit has a power supply, and wherein the lower connection side of each of the plurality of agitator units comprises a power connection connected to the power supply of the base unit.

7. The blood platelet storage system of claim 2, wherein each of the plurality of agitator units has an access opening for the insertion and removal of platelet concentrates, a door which is openable to provide access to the access opening and closeable to close the access opening, and wherein opening of the door causes movement of the moveable compartment to be stopped.

8. The blood platelet storage unit of claim 3, wherein the blood platelet storage system has a control device, and wherein the control device is configured to actuate the individual drive of each of the plurality of agitator units on an individual basis.

9. The blood platelet storage system of claim 2, wherein the blood platelet storage system further comprises a temperature regulation liquid circuit, wherein the temperature regulation liquid circuit comprises a pump for circulation of a temperature regulation liquid through the temperature regulation liquid circuit and wherein each of the plurality of agitator units has a liquid circuit that is connected to the temperature regulation liquid circuit.

10. The blood platelet storage system of claim 9, where the liquid circuit of each of the plurality of agitator units is connected to the temperature regulation liquid circuit via one or more couplings arranged at a position selected from (a) the lower connection side, (b) the upper connection side, and (c) both the lower connection side and the upper connection side.

11. The blood platelet storage system of claim 2,
wherein the blood platelet concentrates are disposed in bags,
wherein the blood platelet concentrates disposed in bags are arranged in the moveable compartments of each of the plurality of agitator units; and
wherein the blood platelet storage system maintains the blood platelet concentrates disposed in bags at a temperature of about 22° C.±2° C.

12. The blood platelet storage system of claim 1, wherein each of the plurality of agitator units has an individual drive for movement of its respective moveable compartment.

13. The blood platelet storage system of claim 1, wherein each of the plurality of agitator units has an access opening for the insertion and removal of blood platelets, a door which is openable to provide access to the access opening and closeable to close the access opening, and wherein opening of the door causes movement of the moveable compartment to be stopped.

14. The blood platelet storage unit of claim 13, wherein the blood platelet storage system has a control device, and wherein the control device is configured to actuate the individual drive of each of the plurality of agitator units on an individual basis.

15. The blood platelet storage system of claim 1, wherein the blood platelet storage system further comprises a temperature regulation liquid circuit, wherein the temperature regulation liquid circuit comprises a pump for circulation of a temperature regulation liquid through the temperature regulation liquid circuit and wherein each of the plurality of agitator units has a liquid circuit that is connected to the temperature regulation liquid circuit.

16. The blood platelet storage system of claim 1,
wherein the blood platelet concentrates are disposed in bags,
wherein the blood platelets concentrates disposed in bags are arranged in the moveable compartments of each of the plurality of agitator units; and
wherein the blood platelet storage system maintains the blood platelet concentrates disposed in bags at a temperature of about 22° C.±2° C.

* * * * *